United States Patent
Takata et al.

(10) Patent No.: US 11,250,951 B2
(45) Date of Patent: Feb. 15, 2022

(54) FEATURE ENGINEERING METHOD, APPARATUS, AND SYSTEM

(71) Applicant: HITACHI, LTD., Tokyo (JP)

(72) Inventors: Mika Takata, San Jose, CA (US); Hideo Aoki, Santa Clara, CA (US)

(73) Assignee: HITACHI, LTD., Tokyo (JP)

( * ) Notice: Subject to any disclaimer, the term of this patent is extended or adjusted under 35 U.S.C. 154(b) by 278 days.

(21) Appl. No.: 15/942,223

(22) Filed: Mar. 30, 2018

(65) Prior Publication Data

US 2019/0304603 A1 Oct. 3, 2019

(51) Int. Cl.
*G16H 50/20* (2018.01)
*G16H 50/30* (2018.01)
*G16H 10/60* (2018.01)
*G06N 20/00* (2019.01)
*G16H 50/70* (2018.01)

(52) U.S. Cl.
CPC .............. *G16H 50/20* (2018.01); *G06N 20/00* (2019.01); *G16H 50/30* (2018.01); *G16H 50/70* (2018.01); *G16H 10/60* (2018.01)

(58) Field of Classification Search
CPC ........ G16H 50/20; G16H 50/70; G16H 50/30; G16H 10/60; G06N 20/00
USPC .......................................................... 705/2
See application file for complete search history.

(56) References Cited

U.S. PATENT DOCUMENTS 8,417,715 B1 4/2013 Tilmann et al.
9,489,630 B2 * 11/2016 Achin ...................... G06N 5/04
(Continued)

FOREIGN PATENT DOCUMENTS

JP 2005-49960 A 2/2005
WO WO-2009103156 A1 * 8/2009 .............. G16H 20/70
WO WO-2016013004 A1 * 1/2016 ............ A61B 6/5252

OTHER PUBLICATIONS

M. Hoogendom et al.; Prediction using patient comparison vs. modeling: A case study for mortality prediction, 2016 38th Annual International Conference of the IEEE Engineering in Medicine and Biology Society (EMBC), 2016, pp. 2464-2467, doi: 10.1109/EMBC.2016.7591229 (Year: 2016).*

(Continued)

*Primary Examiner* — Hiep V Nguyen
(74) *Attorney, Agent, or Firm* — Procopio, Cory, Hargreaves & Savitch LLP

(57) ABSTRACT

Example implementations described herein are directed to systems and methods for feature preparation that receives patient feature data and determines similarity of pre-stored models with the patient feature data. In an example implementation, a database of the pre-stored models is analyzed to assess similarity indicating that feature preparation of the pre-stored models is compatible with the patient feature data. For similarity indicative of feature preparation to be utilized, the feature preparation is conducted for the patient feature data based on the pre-stored model determined to be similar. The feature preparation retrieves reusable features associate with the similar pre-stored model, where the reusable features comprise pre-calculated features of the model. A machine learning model is generated using results of the feature preparation and patient feature data; and a prediction is provided using the machine learning model.

14 Claims, 19 Drawing Sheets

(56) References Cited

U.S. PATENT DOCUMENTS

| | | | | |
|---|---|---|---|---|
| 2008/0154821 A1* | 6/2008 | Poulin | ............... | G06Q 10/0631 706/21 |
| 2008/0275733 A1* | 11/2008 | Schmidt | ............... | G06Q 50/22 705/3 |
| 2013/0191158 A1* | 7/2013 | Fillmore | ............... | G16H 50/30 705/3 |
| 2013/0290110 A1* | 10/2013 | LuVogt | ............... | G06F 16/9535 705/14.66 |
| 2015/0006456 A1* | 1/2015 | Sudharsan | ............... | G06N 5/04 706/46 |
| 2017/0011087 A1* | 1/2017 | Hyde | ............... | G06F 16/211 |

OTHER PUBLICATIONS

Extended European Search Report for related European Application No. 19156342.8, dated Aug. 20, 2019; 11 pages.

Vartak, Manasi, et al., "ModelDB: A System for Machine Learning Models Management", Intel Science and Technology Center for Big Data, 3 pages, <istc-bigdata.org/index.php/modeldb-a-system-for-managing-machine-learning-models> Accessed Mar. 26, 2018; Copyright 2016.

Miao, Hui, et al., "Model Hub: Deep Learning Lifecycle Management", pp. 1393-1394; 2017 IEEE 33rd International Conference on Data Engineering, Apr. 19, 2017.

Pan, Sinno Jialin, et al., "A Survey on Transfer Learning", IEEE Transcations on Knowledge and Data Engineering, 15 pages, vol. 22, Issue Oct. 10, 2010.

Brown, Gavin, "Ensemble Learning", School of Computer Science, the University of Manchester, United Kingdom. Encyclopedia of Machine Learning (Eds), Springer Press 2010, 24 pages.

Office Action for corresponding Japanese application No. 2019-030095 dated Feb. 13, 2020; English translation provided (16 pages).

Communication Pursuant to Article 94(3) for related European Patent Application No. 19156342.8 dated Jun. 25, 2020 (11 pages).

\* cited by examiner

501 SIMILAR MODEL LIST

Model_name, id, reusable data-source, reusable features, reusable features path, similarity
Model A, 1,[/home/user1/poc_data/med.txt,/home/user1/poc_data/lab.txt, /home/user1/poc_data/note.txt],
[table1.A,table1.B,table2.C,table2.D,table3.Note_A],
[/home/user1/poc_data/med.txt,/home/user1/feature.h5],
0.8

FIG. 5A

502 SIMILAR MODEL LIST

Model_name, id, reusable data-source,reusable features, reusable features path, similarity, user's selection
Model A1, 1 ,[/home/user1/poc_data/med.txt,/home/user1/poc_data/labA.txt],
[table1.A,table1.B,table2.C,table2.D,Note A],
[/home/user1/poc_data/med.txt,/home/user1/featureA1.h5],
0.8,0
Model A2, 2 ,[/home/user1/poc_data/med.txt,/home/user1/poc_data/labA.txt],
[table1.A,table1.B,table2.C,table2.D,Note A,Note B],
[/home/user1/poc_data/med.txt,/home/user1/featureA2.h5],
0.5,1

FIG. 5B

| Name | id | Feature name | features | Feature Lineage | algorithm | Tuning parameter | Weight parameter | Feature pointer | Data source pointers | Operator | Created date |
|---|---|---|---|---|---|---|---|---|---|---|---|
| Model A | 1 | Feature A | [pid, med_A, lab_A, Note_A] | {pid:/home/hdfs:// localhost:9000/ patient_data1/ pid,med_A:if(hdfs:/ //localhost:9000/ user/mt/ patient_data1/ med1,hdfs:// localhost:9000/ user/mt/ patient_data1/ med2),...} | Deep learning_S | T1 | W1 | /home/ mt/ features A.h5 | [hdfs:// localhost:9000/ user/mt/ patient_data1.hdfs ://localhost:9000/ user/mt/ med_data1.hdfs:// localhost:9000/ user/mt/ lab_data1.hdfs:// localhost:9000/ user/mt/noteA] | Transformation1. ktl | 2017-12-12 10:00:00.000 |
| Model C | 3 | Feature C | [pid, medX, medY, labX,...] | {pid:/home/hdfs:// localhost:9000/ user/mt/ patient_data1/ pid,...} | Deep learning_S | T1 | W3 | /home/ mt/ features B.h5 | [hdfs:// localhost:9000/ user/mt/ patient_data1.hdfs ://localhost:9000/ user/mt/data2,...] | Transformation2. ktl | 2017-10-12 10:00:00.000 |

| Name | id | Feature name | features | Feature Lineage | algorithm | Tuning parameter | Weight parameter | Feature pointer | Data source pointers | Valid start date | Valid end date | Valid end date | # of Samples | Recipe | Created date |
|---|---|---|---|---|---|---|---|---|---|---|---|---|---|---|---|
| Model A | 1 | Feature A | {pid, med_A, lab_A, Note_A} | {pid:/home/ hdfs:// localhost:9000/ user/mt/ patient_data1/ pid,med_A:{hdfs ://localhost:9000/ user/mt/ med1.hdfs:// localhost:9000/ user/mt/ patient_data1/ | Deep learning_s | T1 | W1 | /home/ mt/ features A.h5 | [hdfs:// localhost:9000/ user/mt/ patient_data1,hd fs:// localhost:9000/ user/mt/ med_data1,hdfs: //localhost:9000/ user/mt/ lab_data1,hdfs:// localhost:9000/ user/mt/noteA] | 2014/1/1 | 2015/12/31 | 2015/12/31 | 20000 | /home/ expect / recipe. yaml | 2017-12-12 10:00:00 .000 |
| Model C | 3 | Feature C | {pid, medX, medY, labX,...} | {pid:/home/ hdfs:// localhost:9000/ user/mt/ patient_data1/ pid,...} | Deep learning_s | T1 | W3 | /home/ mt/ features B.h5 | [hdfs:// localhost:9000/ user/mt/ patient_data1,hd fs:// localhost:9000/ user/mt/data2,...] | 2013/1/1 | 2015/12/31 | 2015/12/31 | 1000 | /home/ expect / recipe. yaml | 2017-10-12 10:00:00 .000 |

| Patient ID | Med_test1 | Med_test2 | Lab_test1 | Note A |
|---|---|---|---|---|
| CA-0001 | 3.1 | 42.0 | 1 | "He has A symptom…" |
| CA-0002 | 2.0 | 43.0 | 2 | "He has A symptom…" |
| CA-0003 | 1.0 | 40.0 | 3 | "He did X and he got A symptom…" |
| CA-0004 | 2.0 | 40.2 | 2 | "She has Z symptom…" |
| CA-0005 | 1.0 | 20.2 | 1 | "She has Z symptom…" |

| Patient ID | Note B | Note C |
|---|---|---|
| CA-0001 | "He has B symptom…" | "He has C symptom…" |
| CA-0002 | "He has A symptom…" | "He has C symptom…" |
| CA-0003 | "He did X and he got A symptom…" | "He did X and he got A symptom…" |
| CA-0004 | "She has B symptom…" | "She has Y symptom…" |
| CA-0005 | "She has B symptom…" | "She has Y symptom…" |

| Patient ID | Med_test1 | Med_test2 | Lab_test1 | Note A | Note B | Note C |
|---|---|---|---|---|---|---|
| CA-0001 | 3.1 | 42.0 | 1 | "He has A symptom..." | "He has B symptom..." | "He has C symptom..." |
| CA-0002 | 2.0 | 43.0 | 2 | "He has A symptom..." | "He has A symptom..." | "He has C symptom..." |
| CA-0003 | 1.0 | 40.0 | 3 | "He did X and he got A symptom..." | "He did X and he got A symptom..." | "He did X and he got A symptom..." |
| CA-0004 | 2.0 | 40.2 | 2 | "She has Z symptom..." | "She has B symptom..." | "She has Y symptom..." |
| CA-0005 | 1.0 | 20.2 | 1 | "She has Z symptom..." | "She has B symptom..." | "She has Y symptom..." |

FEATURE ENGINEERING METHOD, APPARATUS, AND SYSTEM

BACKGROUND

Field

The present disclosure relates generally to feature preparation for machine learning models, and more specifically, to a model management method, apparatus, and system for feature preparation with reusable features.

Related Art

Related art implementations involve data preparation in end-to-end machine learning and analysis. Machine learning using large amounts of raw data traditionally requires substantial resources to pre-process the raw data into trained models. In related art implementations, individually trained models independently prepare data for cases with different types of data. Since each case can have different raw data from different data sources, the data may be incomplete or lack common data causing repetitive and inaccurate data preparation. Further, related art implementations require time-consuming ad-hoc feature engineering changes in the data.

In a related art example, different health care data for individual patients of a hospital is separately pre-processed to create individually trained models to predict health needs. However, separately pre-processing raw data and maintaining individual patient models with related art implementations is resource intensive and time-consuming. Further, related art implementations need models to be re-trained as the data and data sources change.

In other related art implementations, a generalized model can be trained using an aggregate of data from different patients that is less accurate and potentially dangerous for predicting health needs. For example, diagnosing patients using a generalized model trained from an aggregate of patient data cannot be tailored to accurately diagnose an individual patient. Moreover, the originating data sources used to create a trained model are typically unidentifiable in related art machine learning tools.

BRIEF DESCRIPTION OF DRAWINGS

FIGS. 5A and 5B illustrate example similar model lists in accordance with example implementations.

FIGS. 13A and 13B illustrate example model metadata in accordance with example implementations.

FIG. 14 illustrates an example table of reusable features in accordance with an example implementation.

FIG. 15 illustrates an example table of non-pre-stored features in accordance with an example implementation.

FIG. 16 illustrates an example table of new features in accordance with an example implementation.

SUMMARY

Figure 1:
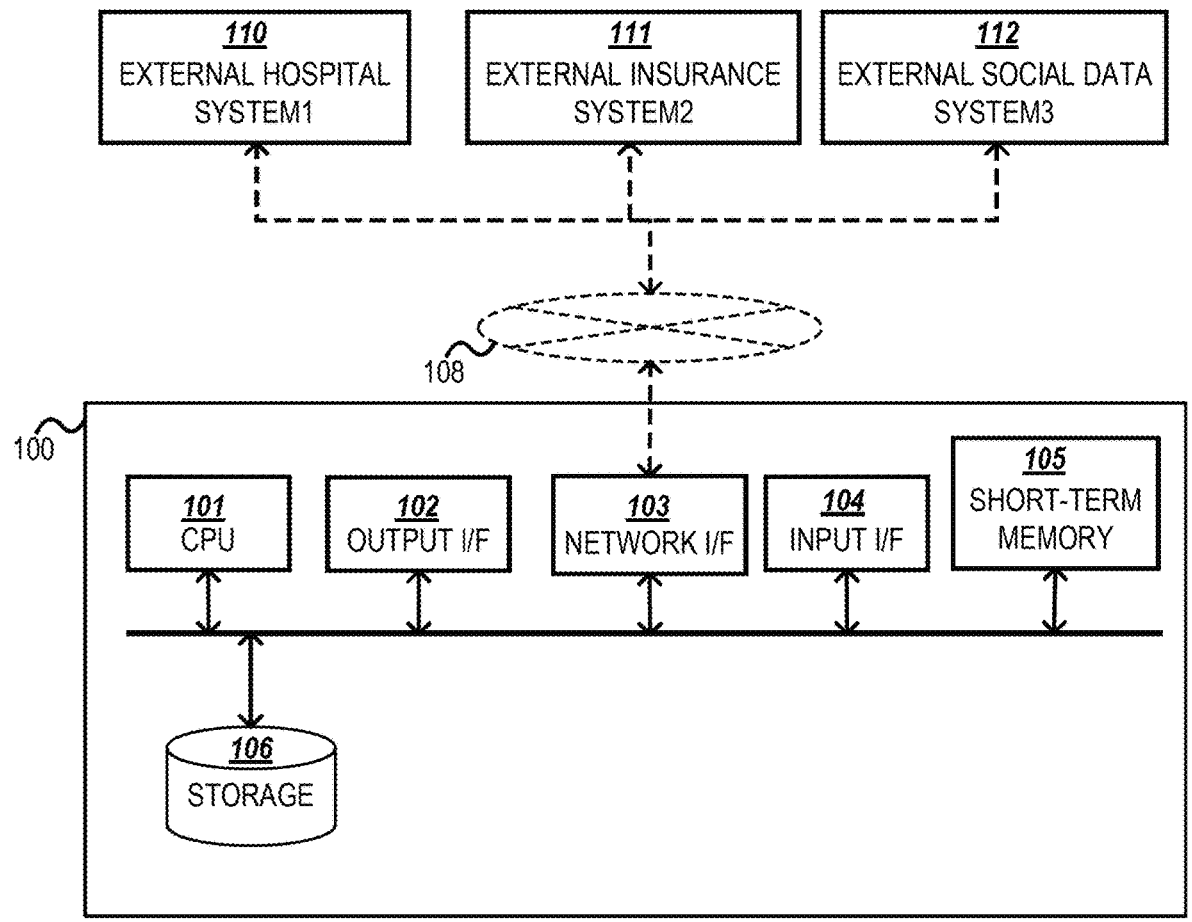
FIG. 1 illustrates an example hardware configuration for a model management system in accordance with an example implementation.

Aspects of the present disclosure can include a method for feature preparation that receives patient feature data and determines similarity of pre-stored models with the patient feature data. A database of the pre-stored models is analyzed to assess similarity indicating that feature preparation of the pre-stored models is compatible with the patient feature data. For similarity indicative of feature preparation to be utilized, the feature preparation is conducted for the patient feature data based on the pre-stored model determined to be similar. The feature preparation retrieves reusable features associate with the similar pre-stored model, where the reusable features comprise pre-calculated features of the model. A machine learning model is generated using results of the feature preparation and patient feature data; and a prediction is provided using the machine learning model.

Aspects of the present disclosure can include a system with a memory and processing device configured to perform feature preparation including, to receive patient feature data and determines similarity of pre-stored models with the patient feature data. For example, similarity can be determined based on comparison or distance calculations of all metadata vectors including features, data lineage, amount of data, data distribution, data skew between positive and negative samples, etc. The processing device is configured to analyze a database of the pre-stored models to assess similarity indicating that feature preparation of the pre-stored models is compatible with the patient feature data. For similarity indicative of feature preparation to be utilized, the processing device conducts the feature preparation for the patient feature data based on the pre-stored model determined to be similar. The feature preparation retrieves reusable features associate with the similar pre-stored model, where the reusable features comprise pre-calculated features of the model. The processing device is configured to generate a machine learning model using results of the feature preparation and patient feature data; and provide a prediction using the machine learning model.

Aspects of the present disclosure can include a non-transitory computer readable medium storing instructions for feature preparation that include receiving patient feature data and to determine similarity of pre-stored models with the patient feature data. The instructions analyze a database of the pre-stored models to assess similarity indicating that feature preparation of the pre-stored models is compatible with the patient feature data. For similarity indicative of feature preparation to be utilized, the instructions conduct the feature preparation for the patient feature data based on the pre-stored model determined to be similar. The feature preparation retrieves reusable features associate with the similar pre-stored model, where the reusable features comprise pre-calculated features of the model. The instructions generate a machine learning model using results of the feature preparation and patient feature data; and provide a prediction using the machine learning model.

Aspects of the present disclosure can include a means for feature preparation with means for receiving patient feature data, determining similarity of pre-stored models with the patient feature data, and means for analyzing a database of the pre-stored models to assess similarity indicating that feature preparation of the pre-stored models is compatible with the patient feature data. For similarity indicative of feature preparation to be utilized, means for conducting the feature preparation for the patient feature data based on the pre-stored model determined to be similar are included. The feature preparation includes means for retrieving reusable features associate with the similar pre-stored model, where the reusable features comprise pre-calculated features of the model; means for generating a machine learning model using results of the feature preparation and patient feature data; and means for providing a prediction using the machine learning model.

DETAILED DESCRIPTION

The following detailed description provides further details of the figures and example implementations of the present application. Reference numerals and descriptions of redundant elements between figures are omitted for clarity. Terms used throughout the description are provided as examples and are not intended to be limiting. For example, the use of the term "automatic" may involve fully automatic or semi-automatic implementations involving user or administrator control over certain aspects of the implementation, depending on the desired implementation of one of ordinary skill in the art practicing implementations of the present application. Selection can be conducted by a user through a user interface or other input means, or can be implemented through a desired algorithm. Example implementations as described herein can be utilized either singularly or in combination and the functionality of the example implementations can be implemented through any means according to the desired implementations.

In an example implementation, a health care provider (e.g., a hospital, a doctor, an insurance company, a physical therapist, etc.) can quickly generate a prediction for a patient using sufficiently similar pre-calculated features with minimal pre-processing of data. In an example implementation, a user interface provides a dataset for tests associated with the machine learning model. The interface allows users to selectively include certain test datasets from different sources such as structured patient datasets, medical datasets, lab datasets, as well as unstructured doctor's note dataset.

Described herein is a model management system to control pre-stored models, data sources, operators, and features for pre-calculated model for use with machine learning. Data preparation is generally the most time-consuming part in end-to-end machine learning and analysis. The model management system enables scalable modeling for machine learning on large amounts of different types of data from different sources. Example aspects of the model management system avoids re-training each model for different data subjects or data changes and reduces the number of trained models that need to be stored to service a large number of data subjects. For example, a hospital can efficiently generate accurate treatment predictions for each patient with machine learning models without needing to store and pre-process a trained model for each and every patient.

The model management system determines similarity of pre-stored models with new or requested data and reuses available pre-calculated features for new training to save time and resources. Pre-stored models and pre-calculated features can be combined with newly created models and features to generate machine learning models. The model management system enables fast model preparation for individualized models that accurately predict treatment for different patient by reusing pre-calculated features.

An example aspect of the present disclosure includes a user interface for interacting with the model management system, output of the predictions, and data sources associated with the underlying data of the models. In an example implementation, the user interface provides the user options to configure the feature preparation, receive the results of the machine learning model, and interact with traceable training datasets. The user interface provides visibility into the underlying data while greatly simplifying the ability to trace the raw data used for a prediction back to the various originating data sources. Further, the model management system allows decision makers to interact with the prediction results by using that training model as well as data lineage to identify data sources.

FIG. 1 illustrates an example hardware configuration for a model management system in accordance with an example implementation. An example hardware configuration can include computing device 100 with one or more Central Processing Units (CPU), cores, or processors 101, interfaces (e.g., an output interface (I/F) 102, a network interface 103, an input interface 104), storage (e.g., short-term memory 105, data storage 106, RAM, ROM, and/or the like), any of which can be coupled on a communication mechanism or bus for communicating information or embedded in a computer device.

According to an example implementation, the computing device 100 is operatively coupled to a communication network 108 (e.g., local area network (LAN), a wide area network (WAN), etc.) to connect to one or more external systems (e.g., external hospital system1 110, an external insurance system2 111, an external social data system3 112) to send and receive data used with the model management system.

In an example, the computing device 100 executes the model management system to generate machine learning models that output predictions for health care needs of a patient. The model management system can receive large volumes of data from a variety of different data sources (e.g., the external hospital system1 110, the external insurance system2 111, the external social data system3 112, etc.) to store pre-processed data that can be reused for new patient requests with similar data.

Figure 2:
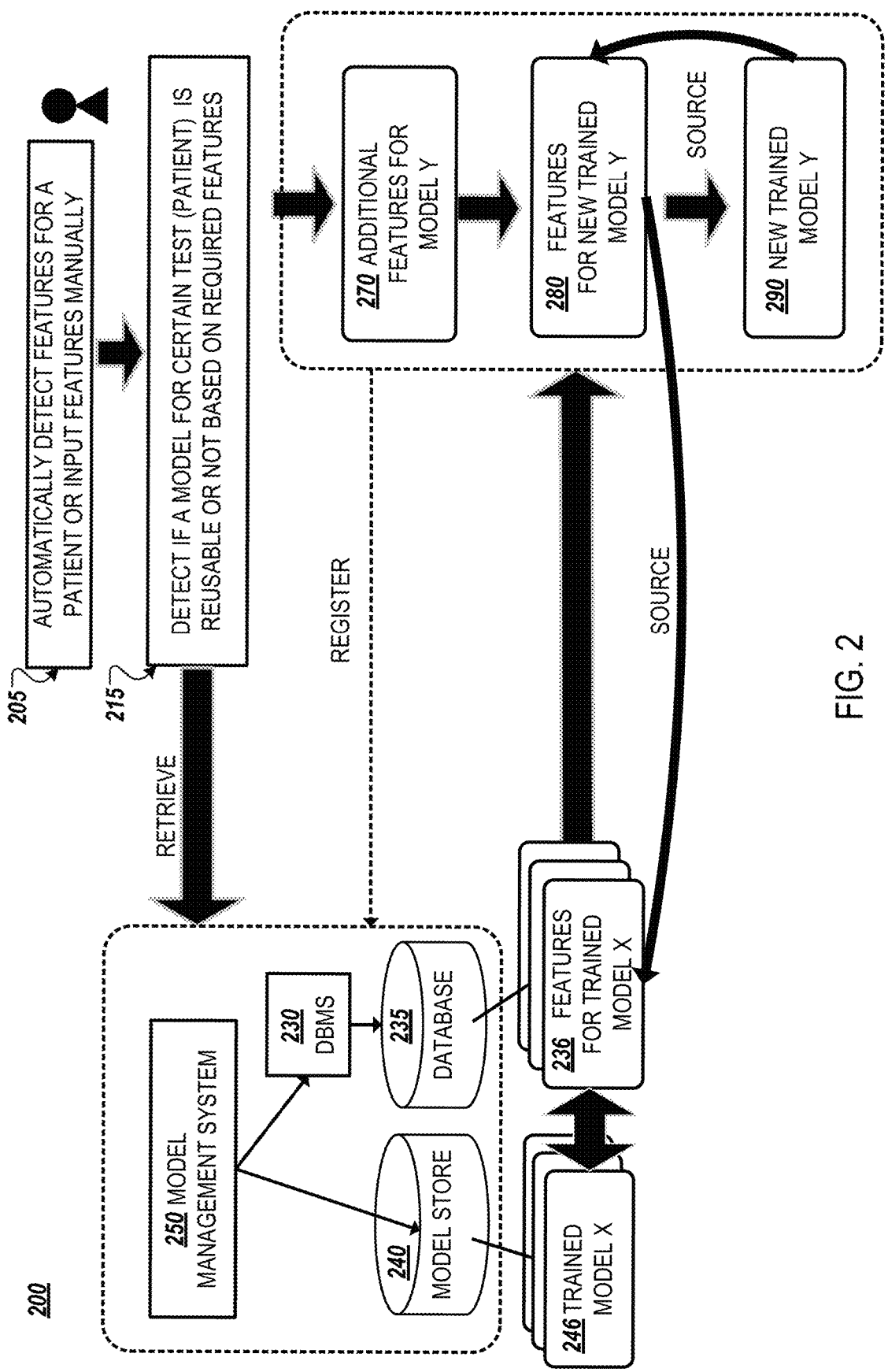
FIG. 2 illustrates an example feature preparation process in accordance with an example implementation.

In an example implementation, the model management system conducts a feature preparation process 200 of FIG. 2 in response to receiving a request for a particular patient or data subject. The request can identify the patient and include raw patient data or the patient data can be gathered from multiple external sources (e.g., the external hospital system1

110, the external insurance system2 111, the external social data system3 112, of FIG. 1).

FIG. 2 illustrates an example feature preparation process 200 in accordance with an example implementation. At 205, the process can retrieve or detect features for the patient from raw patient data. At 215, the process detects if a model for the patient exists that is reusable. The model management system 250 can search a model store 240 to locate a previously stored trained model 246 and features for the trained model 236 from the database 235.

As collected data variety and size is increased in connected healthcare system, each patient can be at different data collection level. For data without any standards, requirements, or structure, the model management system can tune parameters to accurately generate predictions. For example, some data points may be unstructured and inconsistently recorded leaving gaps. Some doctors are likely to keep freeform notes for each patient, while other doctors might not record any patient notes. Doctors' notes are generally useful to recognize and predict the future condition of a patient. The model management system can include a training model to apply the doctor's notes associated with the patient using a more sophisticated model as the note become more sophisticated or detailed. Private patient health data may be in different types, accessibility, and forms (e.g., a smart phone health app). The model management system can receive and track data from a large variety of data sources and process the data in a private training model.

The model management system 250 can also determine if a sufficiently similar model from the model store 240 is reusable based on the features for the patient. If a previously stored model is not detected or outdated, the feature preparation process 200 can create a new model at 270-290. Features from a trained model X 236 with features for the patient from raw patient data 270 can be combined at 280 to create a newly trained model Y 290. The new model can be created 290 from similar models 246 and pre-calculated features of trained model 236. The features for the patient from raw patient data that were not part of the previously stored model can be extracted at 270 and added as additional features for creating a new model at 280. The feature preparation process 200 can also register the additional features in the database 235 to be reused for a later request.

An example method for feature preparation receives patient feature data and determines similarity of pre-stored models with the patient feature data. In an example implementation, a database of the pre-stored models is analyzed to assess similarity indicating that feature preparation of the pre-stored models is compatible with the patient feature data. For example, similarity can be determined based on comparison or distance calculations of all metadata vectors including features, data lineage, amount of data, data distribution, data skew between positive and negative samples, etc. In an example implementation, a similar model list is output includes a model name, a model identifier, a reusable data source, a reusable features, a reusable features path, and a similarity score. In another example implementation, a similar model list is derived from pre-stored models, where the similar model list comprises a user selection for training models. For similarity indicative of feature preparation to be utilized, the feature preparation is conducted for the patient feature data based on the pre-stored model determined to be similar. The feature preparation retrieves reusable features associate with the similar pre-stored model, where the reusable features comprise pre-calculated features of the model. A machine learning model is generated using results of the feature preparation and patient feature data, and a prediction is provided using the machine learning model.

An aspect of the example implementation is described in reference to a health care data to predict patient treatment plans and health diagnosis. In another example implementation, an insurance company can estimate a cost associated with a service based on the prediction results calibrate an appropriate insurance product for the patient. However, the scope of the example implementations is not limited to a specific environment, and other machine learning applications may be substituted therefor without departing from the inventive scope. For example, but not by way of limitation, other machine learning applications in which pre-processed model features can be reused can include real estate, automobiles, insurance, education, recreational applications, but are not limited thereto.

The model management system controls not just pre-stored model but also data sources, operators, and features for pre-calculated models. The model management system enables reuse of pre-calculated features available for new training with newly created new non-rep-calculated features to achieve fast model preparation for each test by effectively reuse pre-calculated features to generate machine learning models and output predictions. The model management system is highly scalable for big data applications, tunes datasets to improve data accuracy, and includes enhanced interactive user tools to explore the results.

Figure 3:
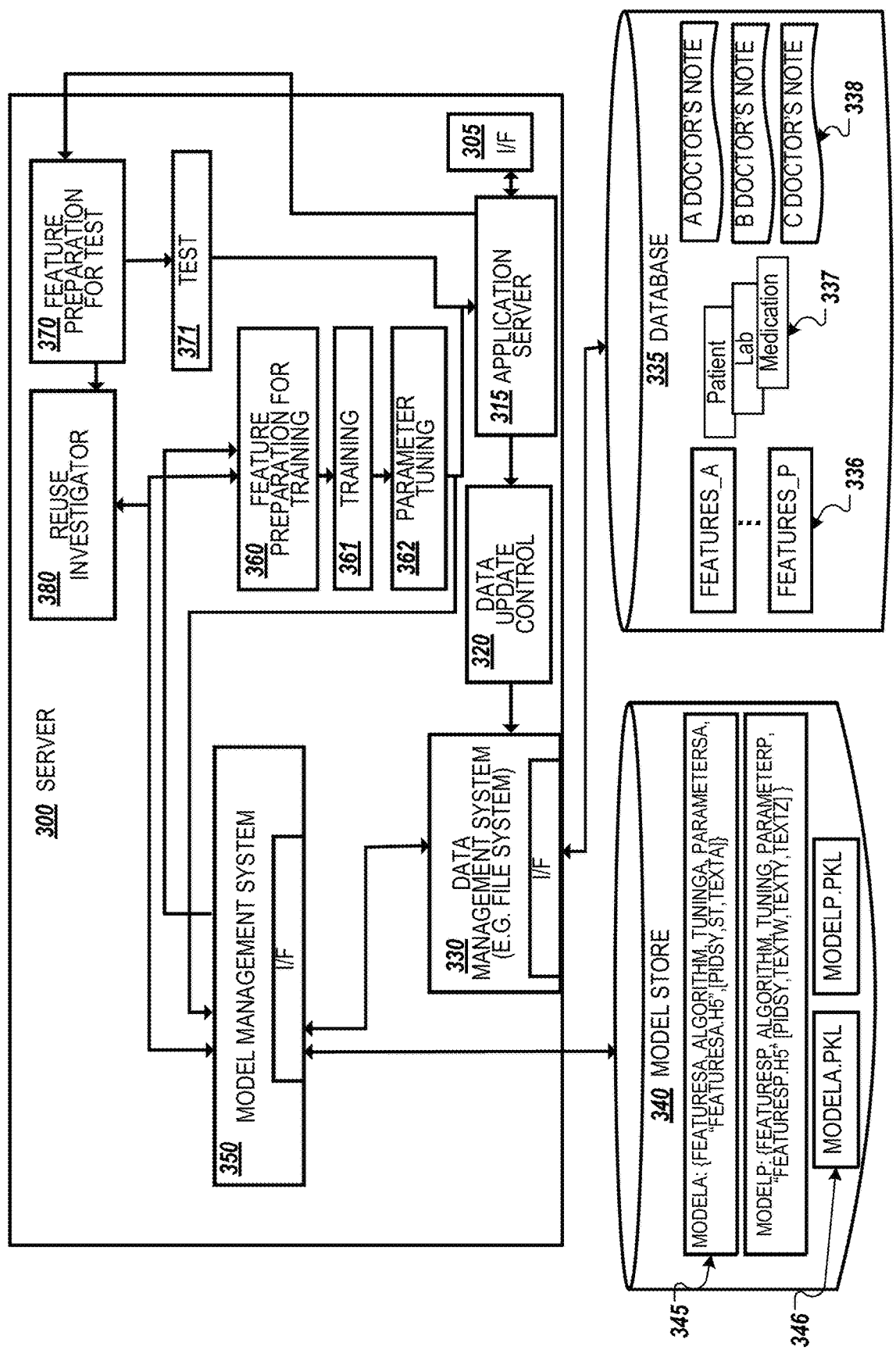
FIG. 3 illustrates an example an example model management server in accordance with an example implementation.

FIG. 3 illustrates an example an example model management server 300 in accordance with an example implementation. The model management server 300 includes components to manage end-to-end model and data management system. In an example implementation, the model management server 300 includes an input interface 305, an application server 315, a data update control module 320, a data management system 330, a model management system 350, a feature preparation for training module 360, a training module 361, a parameter tuning module 362, a feature preparation for test module 370, a test module 371, and a reuse investigator 380.

The model management server 300 can be coupled to a models store 340 to store trained model 346 in various formats (e.g., a pickle file format .pkl) with metadata 345 to describe the trained models. A database 335 stores pre-calculated features 336 with raw data such as structured data 337 (e.g., patient data, lab data, medication data, etc.), and unstructured data 338 (e.g., doctors' notes for patients).

Figure 4:
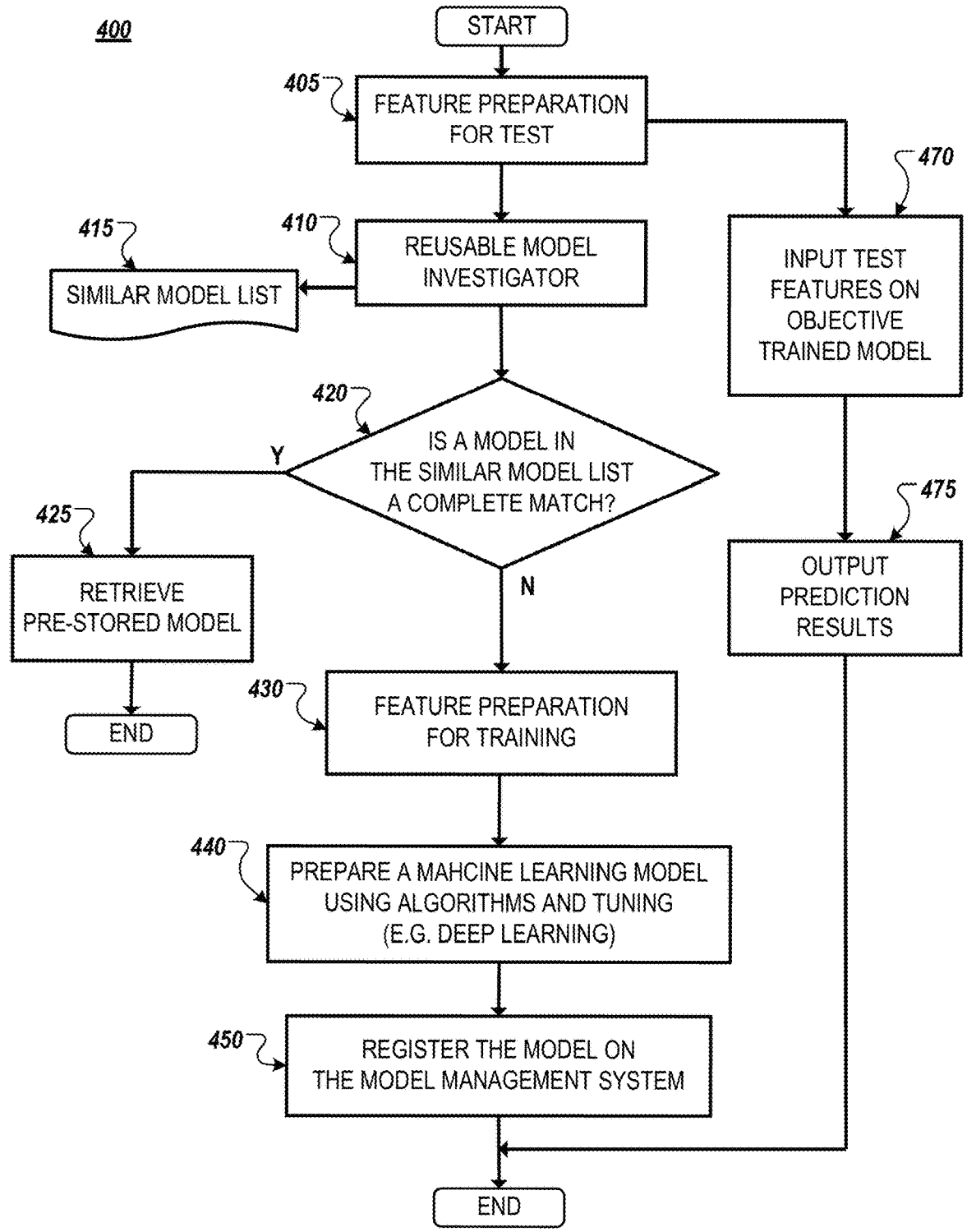
FIG. 4 illustrates an example flow of reusable feature preparation process in accordance with an example implementation.

FIG. 4 illustrates an example flow of reusable feature preparation process 400 in accordance with an example implementation. The process 400 is performed by processing logic that may comprise hardware (circuitry, dedicated logic, etc.), software (such as is run on a general purpose computer system or a dedicated machine), or a combination of both. Process 400 may be performed by a CPU 101 running on server 100 of FIG. 1. Process 400 may also be performed by other processing logic.

The reusable feature preparation process 400 (e.g., feature preparation process 200 of FIG. 2) that can be administered using a model management server (e.g., model management server 300 of FIG. 3). In an example, when a new patient is hospitalized, the new patient may need various types of predictions such as readmission probability, heart disease assessment, or diabetes risk. The prediction output of the process 400 informs the hospital manager and doctors of those risks associated with each assessment for the patient, the treatment can be adjusted (e.g., prioritized, altered, mitigated, controlled, etc.).

In an example implementation, a patient can be identified as test data via input from an interface. The patient test features are automatically extracted, or manually extracted by a system engineer or analyst in the feature preparation for test component. At block 405, the processor conducts a feature preparation for a test to detect received features to be used and set-up feature metadata. At block 410, the reusable model investigator searches a model store to determine similarity of previously stored models with the features from the test. The reusable model investigator determines if this system can reuse some models or features to prepare an appropriate training model for the test data.

FIGS. 5A and 5B illustrate example similar model lists in accordance with example implementations. Each of FIGS. 5A and 5B is an example of similar model list which is derived from reusable model investigator as described in FIG. 4. FIG. 5A illustrates an example similar model list that includes a model name, identifier, reusable data sources, reusable features, reusable features path, and similarity between pre-stored model and test in columns. FIG. 5B is another example of similar model list which has additional user's selection column compared with FIG. 5A. The columns illustrate a user preference for training models as 0 or 1. The similar model list is derived as output from 410.

The reusable model investigator can determine three different condition types: a) one reusable model is located that is stored in model store and satisfies all of the test data, b) a reusable model is located that is stored in model store that satisfies some of the test data, c) no reusable model is located that satisfies any of the test data.

The results of the determination are output as the similar model list 415. At 420, the process investigator determines if the similar model list includes a pre-stored model that matches the test data. Based on the similar model list as shown FIGS. 5A and 5B, if there is 100% match model on the list, the system retrieves that pre-stored model from model store. In response to determining that a reusable model is located that is stored in model store and satisfies all of the test data, the process retrieves the pre-stored model at 425 and ends.

If there is no 100% match model, then the system attempts feature preparation for training which may include feature data reuse. The system attempts to create the training model by learning the features data with some parameter tuning. Then, once a new training model is created, the system registers the model on model management system.

In response to determining that a reusable model is located that is stored in model store that satisfies some of the test data or no reusable model is located that satisfies any of the test data, the process conducts feature preparation to create a new training model at block 430. Other models maybe not reusable directly but some partial features may be reusable to create a new training model. Reuse model investigator recognize that three condition types and process data model management based on the model store status. Those investigation results are outputted from reusable model investigator component as a similar model list.

At block 440, the process prepares a machine learning model by using certain algorithm and tuning. In an example implementation, determining similarity of pre-stored models includes searching the database of reusable models and features based on keys of data sources and feature metadata, outputting a similar model list with the pre-stored models based on the search results; and in response to determining that a pre-stored model from the similar model list with the maximum similarity satisfies a threshold, returning the similar model list. Further, returning the similar model list in response to determining that the pre-stored model from the similar model list with the maximum similarity satisfies the threshold can include tuning the similar model to remove reusable features that fail to satisfy a minimum population criteria and a sample data distribution criteria.

The minimum population criteria or threshold can be used to remove sample data that improves the accuracy of the prediction. In another example, determining similarity of pre-stored models can include determining that the pre-stored models from the similar model list fail to satisfy the threshold, and the system recommends model options for the user to select, and return a model selection based on a user selected model option.

At block 450, the process registers the model on the model management system. The system can process input test features on objective trained model at 470 and outputs prediction results at 475 in parallel with process at 405. A test is conducted when a training model is prepared and prediction or any analytics results is derived as an output of machine learning.

The process 400 enables fast training model creation by reusing pre-calculated features under management with high accuracy for a particular or certain small number of patient groups. Each patient or hospital can generate independent training models based on a test patient to predict his/her future condition. Independent training models for each patient allows for higher accuracy prediction output than aggregated models.

Figure 6:
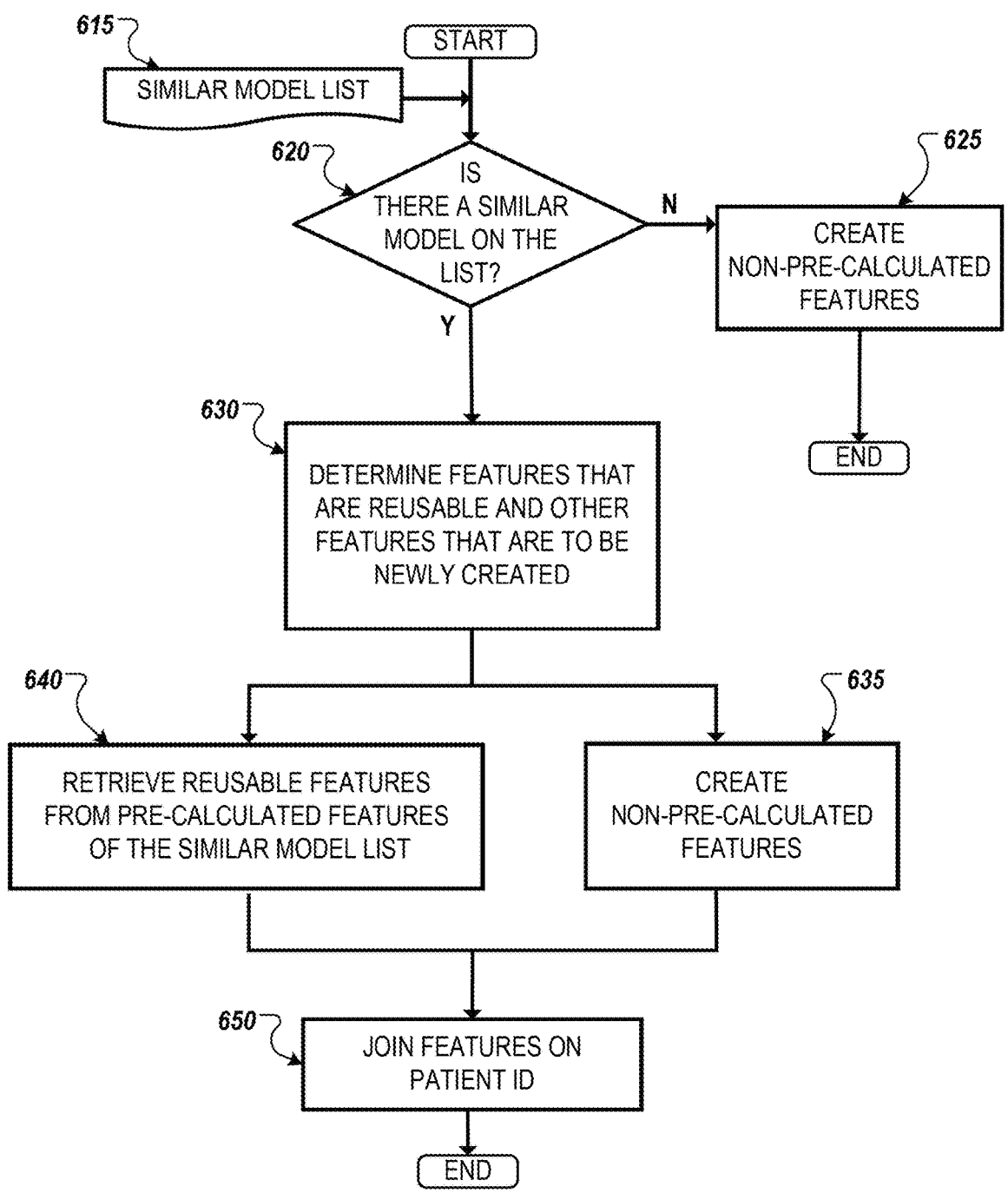
FIG. 6 illustrates an example flow of feature preparation for training in accordance with an example implementation.

FIG. 6 illustrates an example flow of feature preparation for training 600 in accordance with an example implementation. Based on the input of similar model list, as described above, the system prepares features for a training model. If there is no similar model on the similar model list, the system determines to create or extracting new features without using pre-calculated features. When the system determines there is a least one similar model on the similar model list, then the system locates features that are reusable and determines unavailable features that need to be newly created. In an example implementation, the system retrieves the identified reusable features from the database of pre-calculated features, creates the non-pre-calculated features in parallel, and joins features on patient identifier.

In an example implementation, creating non-pre-calculated features for the patient feature data determined not to be similar with pre-stored models; and joining the pre-calculated features and the created non-pre-calculated features with a patient identifier.

At block 615, the process receives the similar model list. At block 620, the process determines if there is a similar model on the list. In response to determining that there is not a similar model on the list, the process creates non-pre-calculated features at block 625. In some example implementations, the database may include a pre-stored model that is partially similar. At block 630, the process determines features that are reusable and other features that are to be newly created. At block 640, the process retrieves the reusable features from pre-calculated features of the similar model list. At block 635, the process creates the non-pre-calculated features needed. At block 650, the process joins the features from blocks 635 and 640 on the patient identifier.

Figure 7:
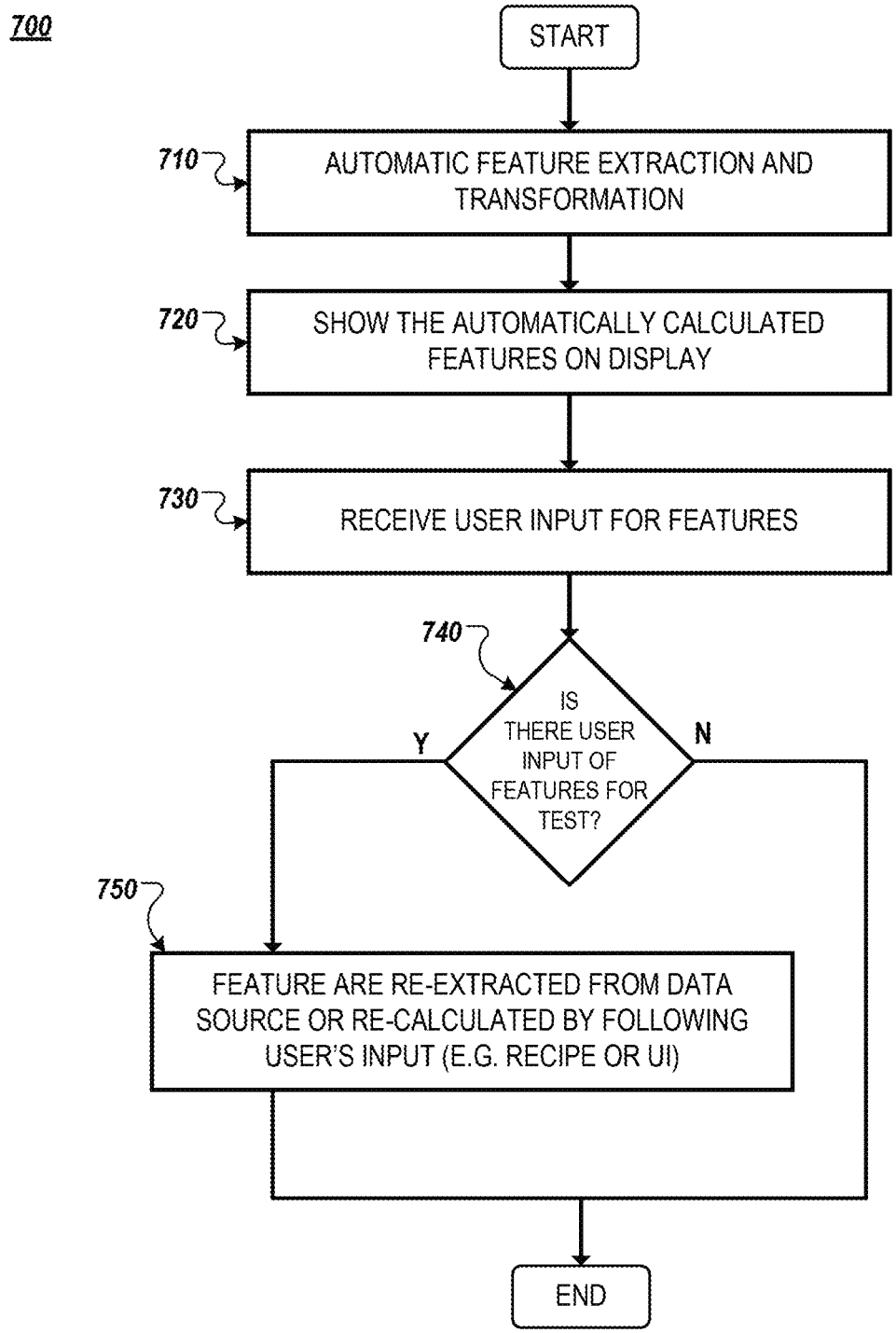
FIG. 7 illustrates an example flow of feature preparation for testing in accordance with an example implementation.

FIG. 7 illustrates an example flow 700 of feature preparation for testing in accordance with an example implementation. At block 710, the process performs automatic feature extraction and transformation. For example, the transformation can be conducted based on metadata associated with the model. A block 720, the process shows the automatically calculated features on a display, such as interface 1700 of FIG. 17. At block 730, the process receives user input for features. At 740, the process determines if there is user input of features for a test. For example, the user can input his/her opinion or preference for the features. The system can execute a user input recipe for the additional feature information for the test. Based on the user input, the process re-extracts features from the data sources or can re-calculate the features based on the user input at block 750.

Figure 8:
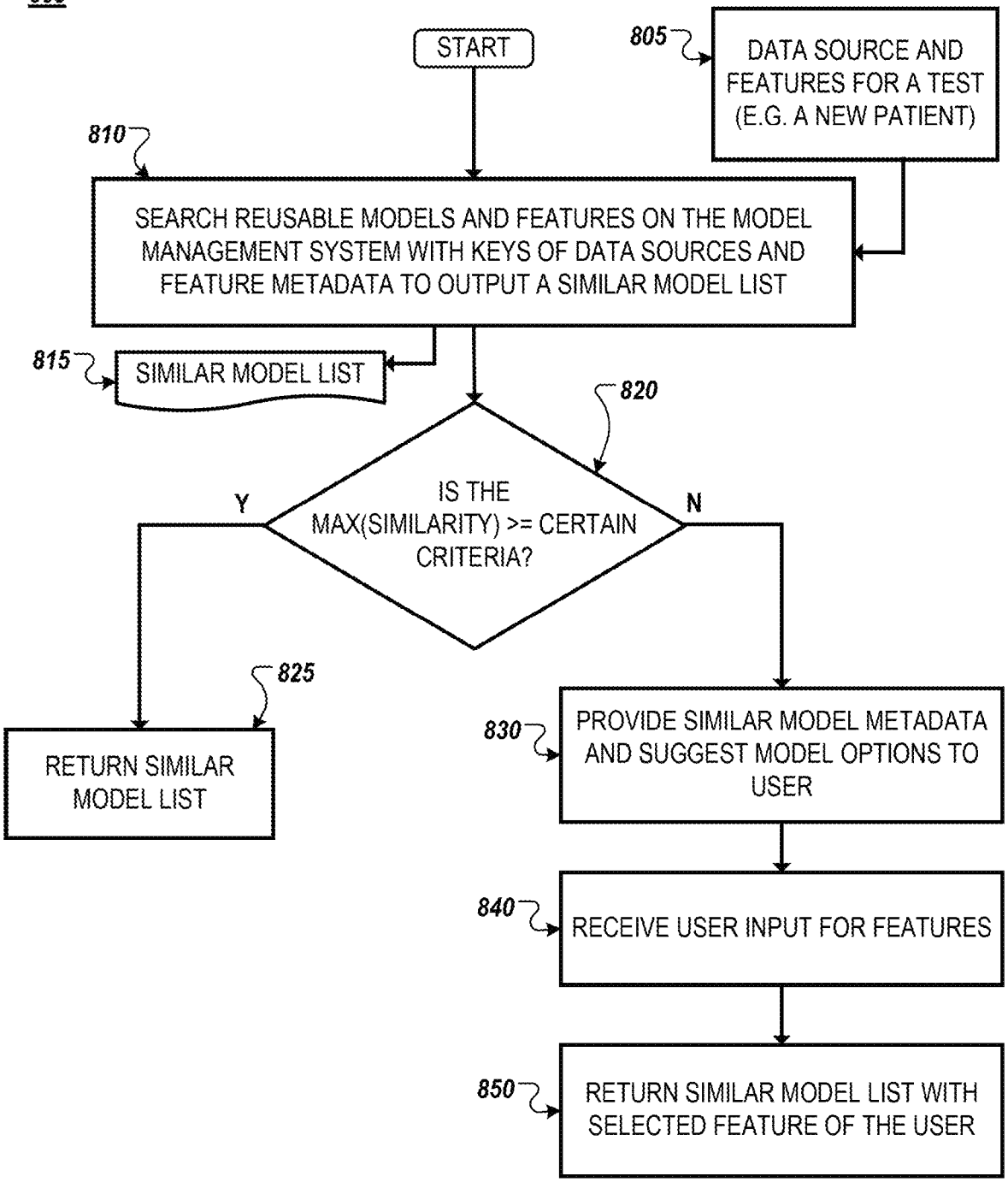
FIG. 8 illustrates an example flow of a reusable model investigation process in accordance with an example implementation.

FIG. 8 illustrates an example flow 800 of a reusable model investigation process in accordance with an example implementation. According to an example implementation, the reusable model investigator can access data sources and features for a test at block 805. At block 810, the reusable model investigator searches the model store using the model management system with keys of data sources and feature metadata. The reusable model investigator outputs the similar model list 815. At block 820, the process determines if there is a model maximum similarity greater than or equal to a certain criteria or threshold. In response to determining that the model with maximum similarity is greater than or equal to the criteria or threshold, the similar model list is returned at 825. When the criteria or threshold is not satisfied, the process proceeds to block 830 to provide similar model metadata and suggest model options to the user. At block 840 the user can select a suggested option or features. If there are no such models on the list, the display shows those low similar model metadata to users and ask them options to use. If some users input their preference, the system accepts the user selection. At block 850 the process returns the similar model list with the selected features of the user.

Figure 9:
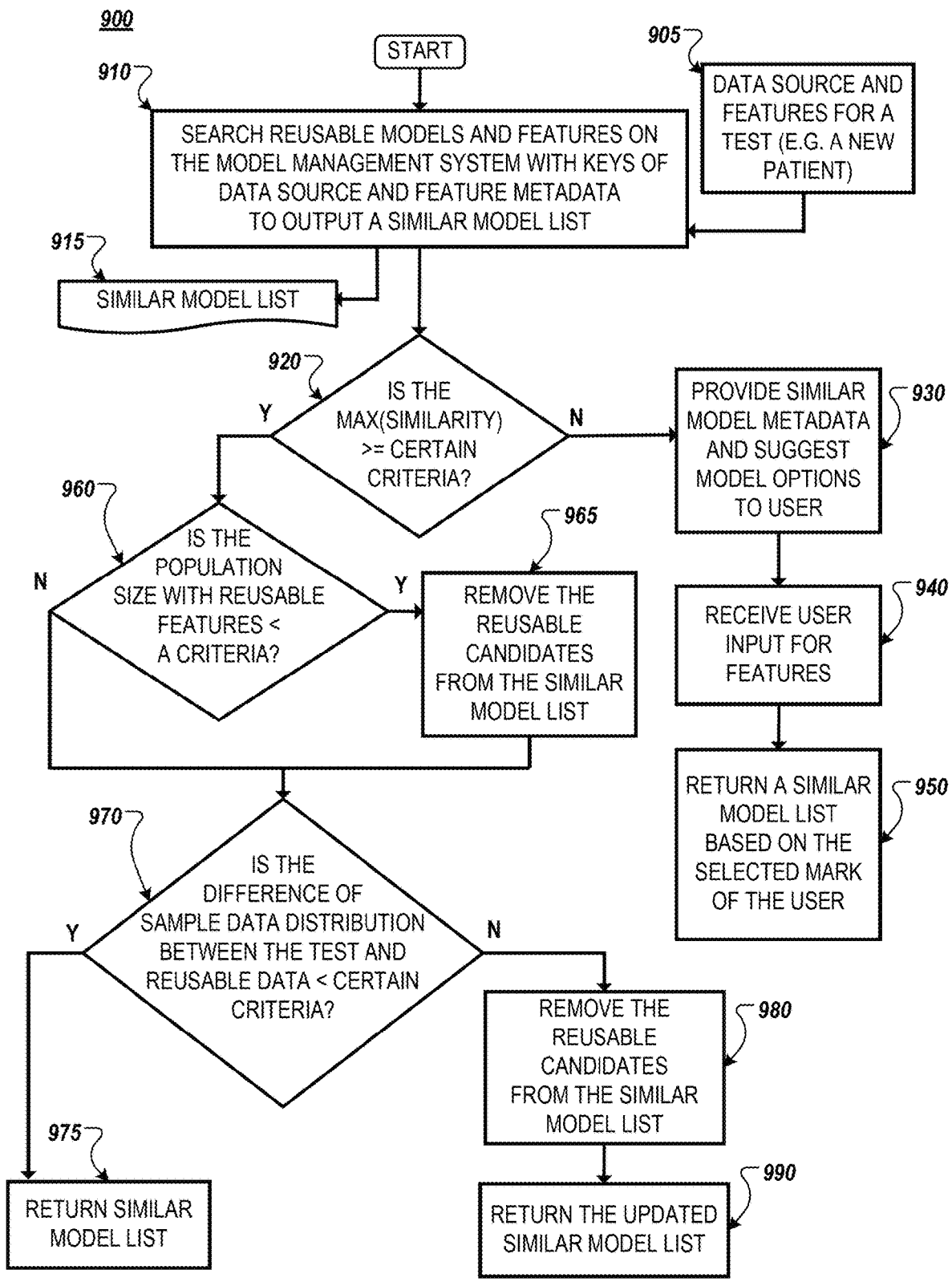
FIG. 9 illustrates an example flow of a reusable model investigation process in accordance with an example implementation.

FIG. 9 illustrates an example flow of a reusable model investigation process in accordance with an example implementation. In another example implementation of the reusable model investigator, the process 900 can return similar model lists with tuning of parameters. Reusable model investigation process 900 removes inappropriate models from the similar model list. A model with the highest similarity rating on the similar model list may have a base population lower than a certain criteria specified for a training model. Further, some training data may be old and might have a much different distribution in the data compared to the test data.

At block 905, data sources and features for a test are received. At block 905, the process searches the model management system keys of the data sources and feature metadata to identify reusable models in features. Based on the search a similar model list is output at 915. At block 920, the process determines if the model with maximum similarity is greater than or equal to a criteria or threshold. In response to determining that the criteria or threshold is not satisfied by the search, the process proceeds to block 930 to provide similar model metadata and suggest model options to the user. At block 940, the process receives user input for suggested model options of the features. At block 950, a similar model list based on the selected mark of the user is returned.

Returning to block 920, when the criteria or threshold is satisfied, the process proceeds to tune parameters from the similar model list. At block 960, the process determines if the population size of the reusable features is less than a size criteria or threshold. In response to the size criteria being greater than the population size with reusable features, the process removes reusable candidates from the similar model list at block 965.

After the reusable candidates are removed from the similar model list at 965 or if the population size is greater than or equal to the size criteria, the process proceeds to block 970. At block 970, the process determines if the difference of the sample data distribution between the test and the reusable data is less than a distribution criteria or threshold. For example, in a lung disease test the patients may have some pre-store model and features with some portion of the data that has totally different data distribution. The different data distribution may indicate the background characteristic has changed completely or is not reliable for the patient (e.g., background characteristic indicates the model is for life long smokers but the pre-stored model includes only non-smoker data).

In response to determining that the difference is less than the distribution criteria, the similar model list is returned at block 975. In response to determining that the difference of the sample data distribution between the test and the reusable data is not less than the distribution criteria, the process removes reusable candidates from the similar model list at block 980. And the similar model list is returned at block 990.

Figure 10:
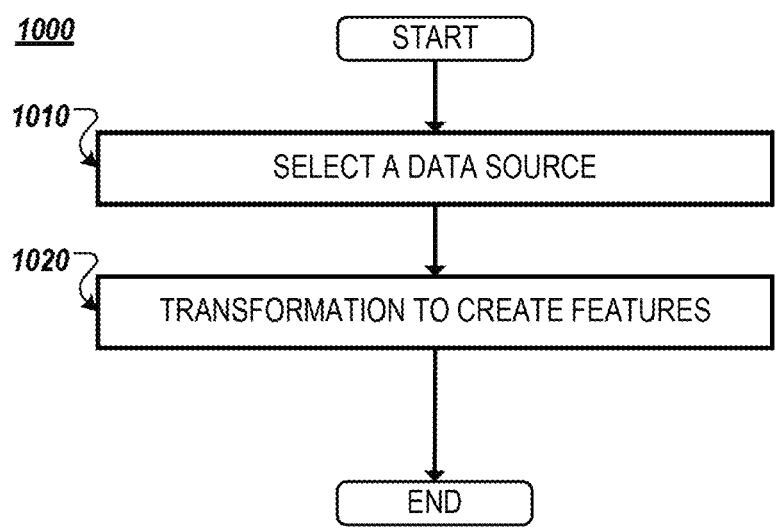
FIG. 10 illustrates an example flow to create non-pre-calculated features in accordance with an example implementation.

FIG. 10 illustrates an example flow 1000 to create non-pre-calculated features in accordance with an example implementation to create appropriate features for a new training model. At block 1010, the process selects a data source. At block 1020, the process transforms to create features.

Figure 11:
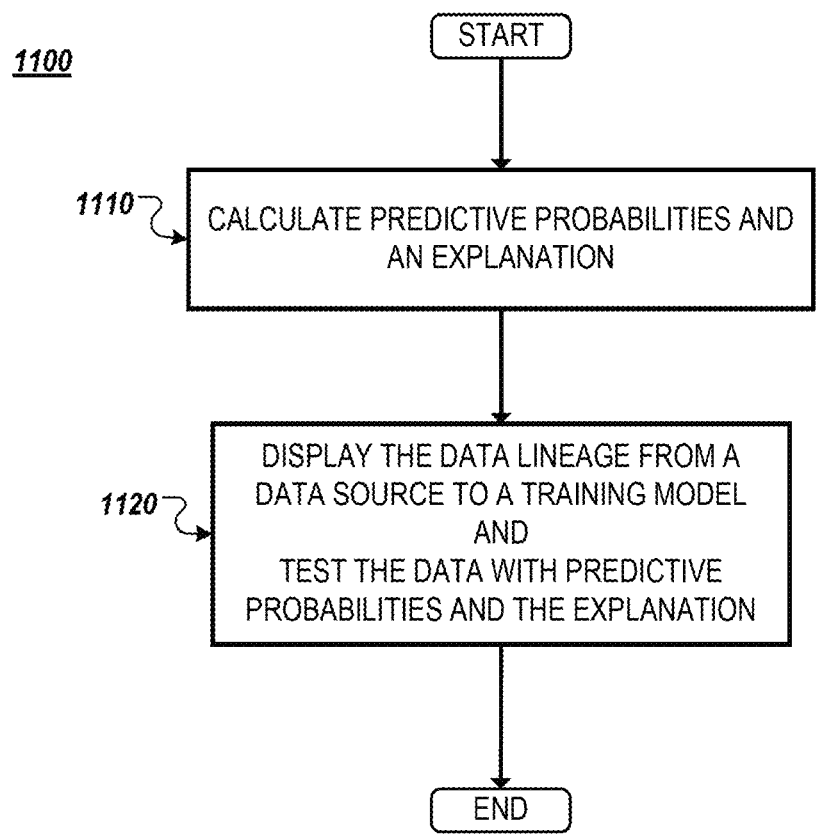
FIG. 11 illustrates an example flow to output prediction results in accordance with an example implementation.

FIG. 11 illustrates an example flow 1100 to output prediction results in accordance with an example implementation. At block 1110, the process calculates predictive probabilities with an explanation. At block 1120, the process displays the data lineage from data sources to training models and test data with predictive probabilities and the explanation. In an example implementation, the data linage is stored as metadata with the model that identifies one or more data sources of data.

The system calculates the predictive probabilities and an explanation for a test features input that is used for training a model. In an example implementation, the prediction is for a future patient condition that is used to form a patient treatment plan. For example, patient data is the test input into the training model, and the system calculates the patient's heart disease risk or readmission probability by using neural networks, support vector machines, random forest or deep learning. The explanation of the analytics can include output for the cause or a factor for the probability. The system can provide the results on the display for users together with the data lineage information to assist with understand and evaluating the prediction results.

Figure 12:
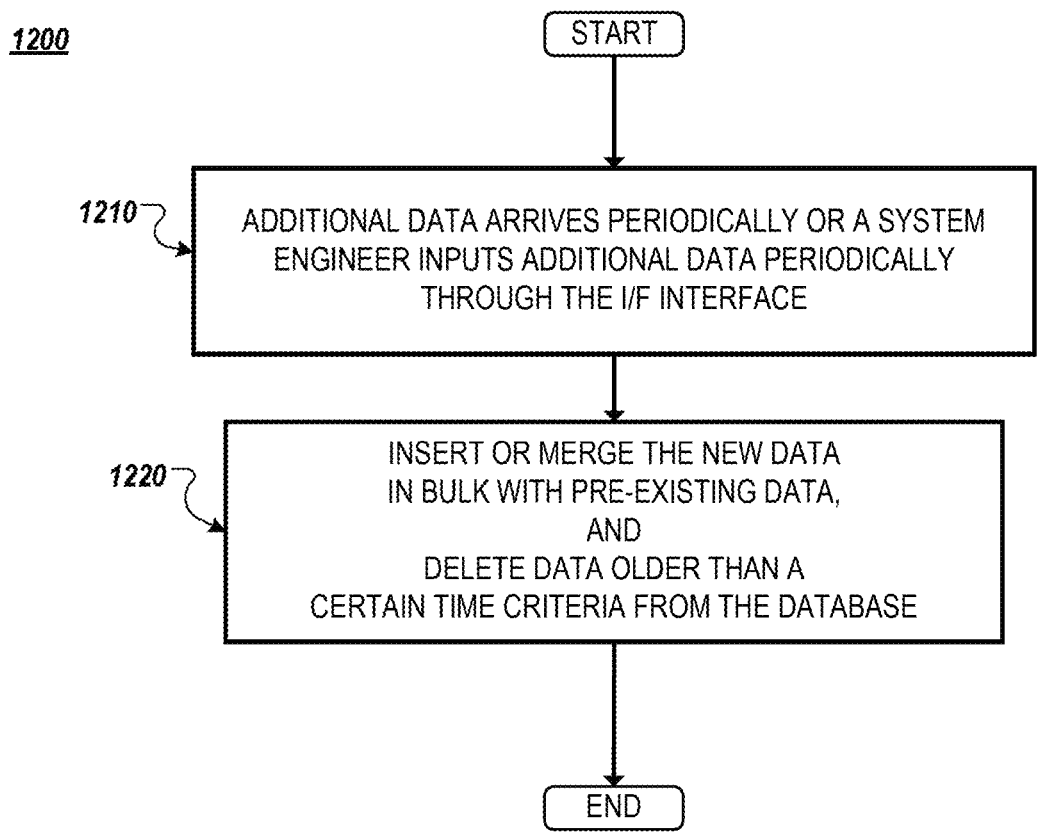
FIG. 12 illustrates an example data update control flow in accordance with an example implementation.

FIG. 12 illustrates an example data update control flow 1200 in accordance with an example implementation. Since the system can connect to external systems, new data can be imported from the external system to the system automatically and/or manually. When additional or new data arrives periodically or a system engineer inputs additional data through the interface, the system can insert the new data in order or merge the new data in bulk with pre-existing data on database. Further, older or stale data can be deleted based on certain criteria (e.g., 10 years from last update).

At block 1210, the process receives additional data periodically or a system engineer can input additional data periodically through an interface. At block 1220, the data update control inserts or merges the new data in bulk with the pre-existing data. According to some example implementations, older data can be deleted or overwritten based on the data becoming stale. The metadata can include, for example, a model name, an identifier, feature name, a listing of the features, a feature lineage, an algorithm used with the model, tuning parameters, weighting parameters, operators, a creation date, etc. For example, the operator metadata can be used to determine the transformation operation for the data preparation. In some example implementations, the metadata can further include data source pointers, valid start date, valid and eight, a number of samples, a recipe, etc.

In an example implementation, valid start dates and end dates can be used to maintain the data with parameter tuning to avoid using stale or outdated data. The metadata can identify a recipe associated with a model to be used during the transformation process. Reusable features can be identified using a patient identifier to associate different types of data, for example structured and unstructured data. The patient identifier can be masked or hashed to anonymize the real identity and protect the privacy of an individual patient.

FIGS. 13A and 13B illustrate example model metadata in accordance with example implementations. FIG. 13A is an example of model metadata to manage model data. The metadata can include, for example, a model name, an identifier, a feature name used for the model, a feature lineage, locations of intermediate files, algorithms used for training, weight parameter for training, feature pointers (e.g., to point out stored location of features by itself), data sources, operators (e.g., describing how to transform and create features from data source and creation date). For example, Model_A with identifier 1 can include Feature_name_A for feature med_A, lab_A, Note_A. The data lineage in the metadata includes a path to identify the data sources. The Model_A is used with Deeplearning_S algorithm, tuning parameter T1, and operator Transformation1.ktl. The metadata can further list the feature point, data source pointers, and various dates associated with the data.

FIG. 13B is another example of model metadata including at least model name, identifier, feature names used for the model, feature lineage, algorithms used for training, weight parameters for training, data sources, valid date periods, a used number of samples, recipe indicating required features and creation date.

FIG. 14 illustrates an example table 1400 of reusable features in accordance with an example implementation. Table 1400 can be created as part of process 600 at block 640 of FIG. 6. As illustrated in table 1400, reusable features for unstructured data can be a doctor's note including freeform text or structured data such as test results with formatted alphanumeric values. For example, 1400 of reusable features can list the patient identifiers CA-0001 through CA-000N and identify reusable features of each patient for Med_test1, Medtest2, Lab_test1, and Note_A. Then patient CA-0004 Medtest2 value 40.2 and Note_A "She has B symptom . . . " can quickly be identified and reused for training a model. Non-pre-calculated features can be created by the system on-the-fly. For example, new data such as doctors' notes can be associated with the patient identifier. For example, reusable feature table includes patient ID, Med_test1 as a type of medication test, Med_test2 for another type of medication test, Lab_test1 for a type of lab test result, and Note A for a doctor A's note for the patient.

FIG. 15 illustrates an example table 1500 of non-pre-stored features in accordance with an example implementation. Table 1500 can be created as part of process 600 at block 635 of FIG. 6. For example, the table 1500 can include a patient identifier, a Note B for a doctor B's note, and a Note C for a doctor C's note.

FIG. 16 illustrates an example table 1600 of new features in accordance with an example implementation. FIG. 16 is an example of new features table 1600 created by using reusable features and non-pre-calculated features. Table 1600 can be created as part of process 600 at block 650 of FIG. 6. Table 1600 is a joined table of reusable features described on FIG. 14 and newly created features described on FIG. 15. Table 1600 can be derived from 650 of FIG. 6. In an example implementation, the non-pre-stored features from Table 1500 for patient CA-0003 with non-pre-stored feature Note C of "He did X and got A symptom . . . " can be joined with reusable features from Table 1400 for patient CA-0003 with Med_test1 2.0.

Figure 17:
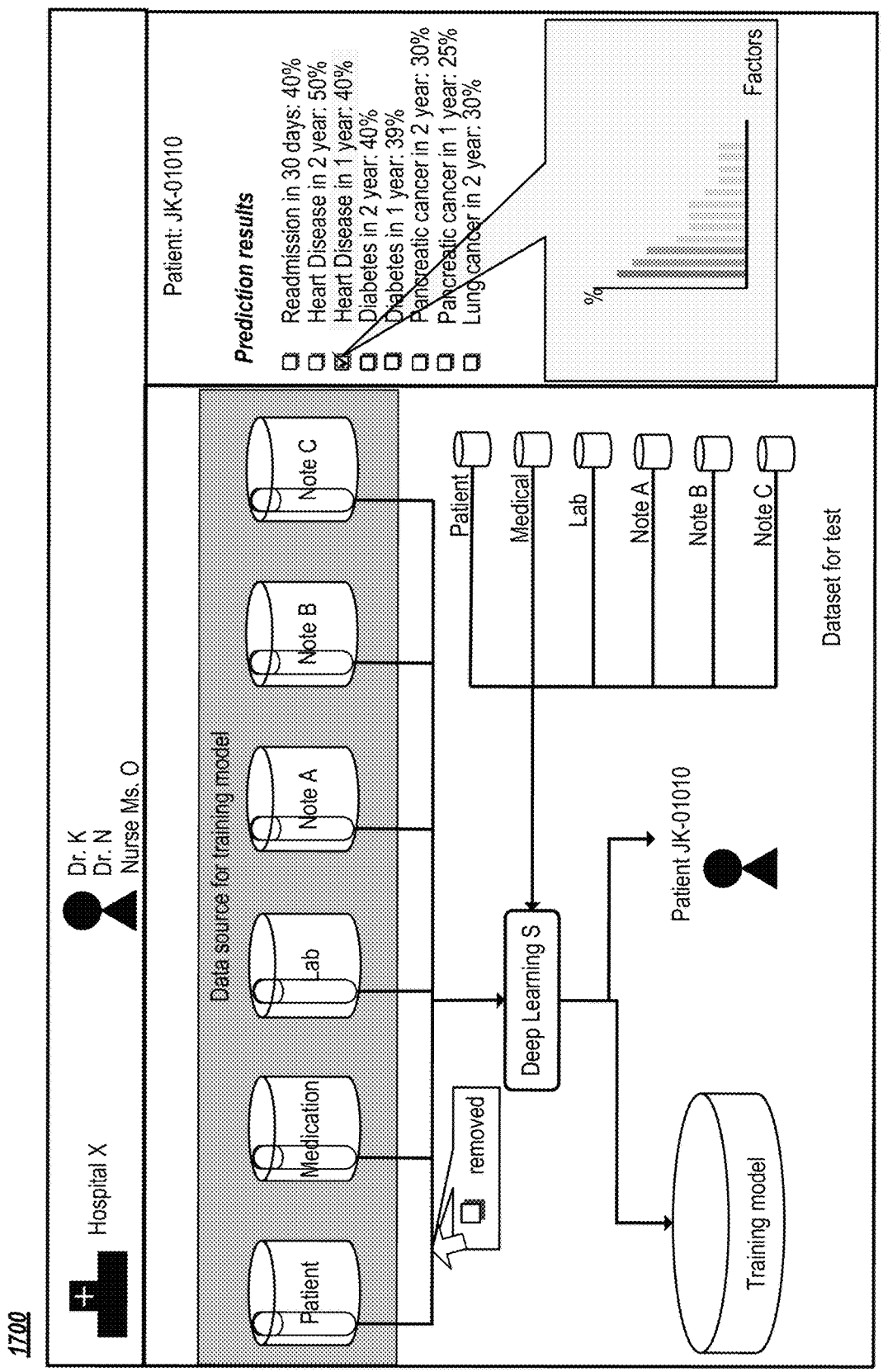
FIG. 17 illustrates an example interface in accordance with an example implementation.

FIG. 17 illustrates an example interface 1700 in accordance with an example implementation. Interface 1700 displays data linkage information, datasets for test, keys, and prediction output results. FIG. 17 is an example image of input and output display for the system users. This is an example dashboard for a certain patient. In an example implementation, the interface 1700 can include a description about a hospital and a doctor team where this patient is treated. The interface 1700 allows for interactive inspection of the data, for example the data lineage allows users to trace the data source for training model. For example, a heart disease prediction can display the data lineage to identify data sources used for the training model from a patient data base, a medication database, a lab database, and doctor's notes databases. According to an example aspect, users can remove certain data source from a training model, for example, by clicking to remove a line on the dashboard of interface 1700.

The interface 1700 includes a display of the methods used in generating the prediction. For example, deep learning S is displayed to inform the user that it was used to create a training model. Further, descriptions of dataset for test patient are shown as a tree from the deep learning S with a patient dataset, a med dataset, a lab dataset, a Note A dataset, a Note B dataset, and Note C dataset.

The interface 1700 provides multiple prediction results as a list with an explanation factors for the prediction on each graph. For example, the predictions results list include a 40% prediction that the test patient will have a readmission in 30 days, a 50% prediction for a heart disease in 2 years, a 40% prediction for a heart disease in 1 year, a 40% prediction for diabetes in 2 years, a 39% prediction for diabetes in 1 year, a 30% prediction for pancreatic cancer in 2 years, a 25% prediction for pancreatic cancer in 1 year, and a 30% prediction for lung cancer in 2 years. Users can be presented with detailed graphs or visual indicators with a visual display of the factors by clicking the result of the list. Users see this display on step 475 on main flowchart shown on FIG. 4.

Figure 18:
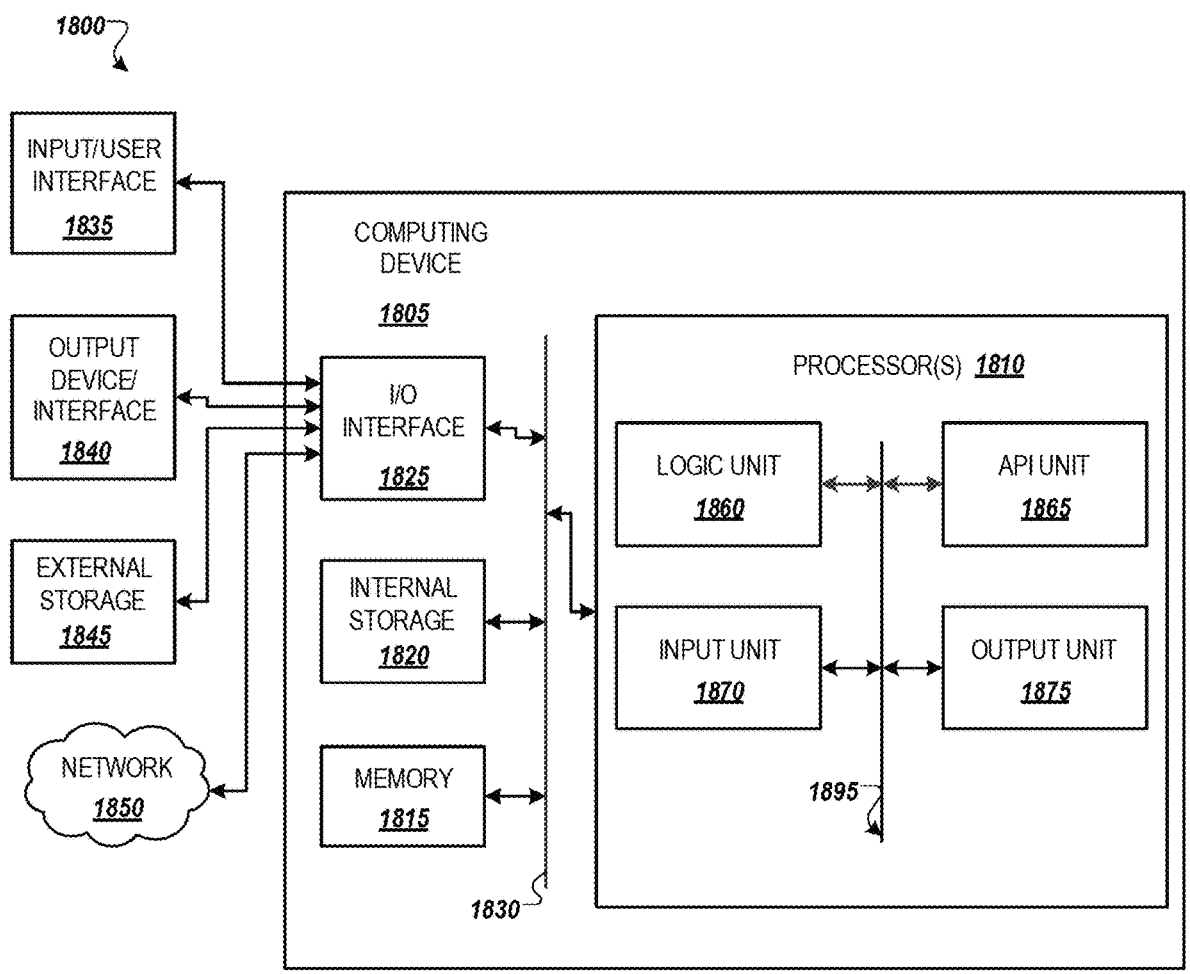
FIG. 18 illustrates an example computing environment with an example computer device suitable for use in some example implementations.

FIG. 18 illustrates an example computing environment with an example computer device suitable for use in some example implementations, such as a model management system 350 as illustrated in FIG. 3. Computer device 1805 in computing environment 1800 can include one or more processing units, cores, or processors 1810, memory 1815 (e.g., RAM, ROM, and/or the like), internal storage 1820 (e.g., magnetic, optical, solid state storage, and/or organic), and/or I/O interface 1825, any of which can be coupled on a communication mechanism or bus 1830 for communicating information or embedded in the computer device 1805. I/O interface 1825 is also configured to receive images from cameras or provide images to projectors or displays, depending on the desired implementation.

Computer device 1805 can be communicatively coupled to input/user interface 1835 and output device/interface 1840. Either one or both of input/user interface 1835 and output device/interface 1840 can be a wired or wireless interface and can be detachable. Input/user interface 1835 may include any device, component, sensor, or interface, physical or virtual, that can be used to provide input (e.g., buttons, touch-screen interface, keyboard, a pointing/cursor control, microphone, camera, braille, motion sensor, optical reader, and/or the like). Output device/interface 1840 may include a display, television, monitor, printer, speaker, braille, or the like. In some example implementations, input/user interface 1835 and output device/interface 1840 can be embedded with or physically coupled to the computer device 1805. In other example implementations, other computer devices may function as or provide the functions of input/user interface 1835 and output device/interface 1840 for a computer device 1805.

Examples of computer device 1805 may include, but are not limited to, highly mobile devices (e.g., smartphones, devices in vehicles and other machines, devices carried by humans and animals, and the like), mobile devices (e.g., tablets, notebooks, laptops, personal computers, portable televisions, radios, and the like), and devices not designed for mobility (e.g., desktop computers, other computers, information kiosks, televisions with one or more processors embedded therein and/or coupled thereto, radios, and the like).

Computer device 1805 can be communicatively coupled (e.g., via I/O interface 1825) to external storage 1845 and network 1850 for communicating with any number of networked components, devices, and systems, including one or more computer devices of the same or different configuration. Computer device 1805 or any connected computer device can be functioning as, providing services of, or referred to as a server, client, thin server, general machine, special-purpose machine, or another label.

I/O interface 1825 can include, but is not limited to, wired and/or wireless interfaces using any communication or I/O protocols or standards (e.g., Ethernet, 802.11x, Universal System Bus, WiMax, modem, a cellular network protocol, and the like) for communicating information to and/or from at least all the connected components, devices, and network in computing environment 1800. Network 1850 can be any network or combination of networks (e.g., the Internet, local area network, wide area network, a telephonic network, a cellular network, satellite network, and the like).

Computer device 1805 can use and/or communicate using computer-usable or computer-readable media, including transitory media and non-transitory media. Transitory media include transmission media (e.g., metal cables, fiber optics), signals, carrier waves, and the like. Non-transitory media include magnetic media (e.g., disks and tapes), optical media (e.g., CD ROM, digital video disks, Blu-ray disks), solid state media (e.g., RAM, ROM, flash memory, solid-state storage), and other non-volatile storage or memory.

Computer device 1805 can be used to implement techniques, methods, applications, processes, or computer-executable instructions in some example computing environments. Computer-executable instructions can be retrieved from transitory media, and stored on and retrieved from non-transitory media. The executable instructions can originate from one or more of any programming, scripting, and machine languages (e.g., C, C++, C#, Java, Visual Basic, Python, Perl, JavaScript, and others).

Processor(s) 1810 can execute under any operating system (OS) (not shown), in a native or virtual environment. One or more applications can be deployed that include logic unit 1860, application programming interface (API) unit 1865, input unit 1870, output unit 1875, and inter-unit communication mechanism 1895 for the different units to communicate with each other, with the OS, and with other applications (not shown). The described units and elements can be varied in design, function, configuration, or implementation and are not limited to the descriptions provided.

In some example implementations, when information or an execution instruction is received by API unit 1865, it may be communicated to one or more other units (e.g., logic unit 1860, input unit 1870, output unit 1875). In some instances, logic unit 1860 may be configured to control the information flow among the units and direct the services provided by API unit 1865, input unit 1870, output unit 1875, in some example implementations described above. For example, the flow of one or more processes or implementations may be controlled by logic unit 1860 alone or in conjunction with API unit 1865. The input unit 1870 may be configured to obtain input for the calculations described in the example implementations, and the output unit 1875 may be configured to provide output based on the predictions described in example implementations. In an example implementation involving a management system configured to feature preparation, as illustrated in the flow diagram of FIG. 4.

Some portions of the detailed description are presented in terms of algorithms and symbolic representations of operations within a computer. These algorithmic descriptions and symbolic representations are the means used by those skilled in the data processing arts to convey the essence of their innovations to others skilled in the art. An algorithm is a series of defined steps leading to a desired end state or result. In example implementations, the steps carried out require physical manipulations of tangible quantities for achieving a tangible result.

Unless specifically stated otherwise, as apparent from the discussion, it is appreciated that throughout the description, discussions utilizing terms such as "determining," "conducting," "generating," "providing," or the like, can include the actions and processes of a computer system or other information processing device that manipulates and transforms data represented as physical (electronic) quantities within the computer system's registers and memories into other data similarly represented as physical quantities within the computer system's memories or registers or other information storage, transmission or display devices.

Example implementations may also relate to an apparatus for performing the operations herein. This apparatus may be specially constructed for the required purposes, or it may include one or more general-purpose computers selectively activated or reconfigured by one or more computer programs. Such computer programs may be stored in a computer readable medium, such as a computer-readable storage medium or a computer-readable signal medium. A computer-readable storage medium may involve tangible mediums such as, but not limited to optical disks, magnetic disks, read-only memories, random access memories, solid state devices and drives, or any other types of tangible or non-transitory media suitable for storing electronic information. A computer readable signal medium may include mediums such as carrier waves. The algorithms and displays presented herein are not inherently related to any particular computer or other apparatus. Computer programs can involve pure software implementations that involve instructions that perform the operations of the desired implementation.

Various general-purpose systems may be used with programs and modules in accordance with the examples herein, or it may prove convenient to construct a more specialized apparatus to perform desired method steps. In addition, the example implementations are not described with reference to any particular programming language. It will be appreciated that a variety of programming languages may be used to implement the teachings of the example implementations as described herein. The instructions of the programming language(s) may be executed by one or more processing devices, e.g., central processing units (CPUs), processors, or controllers.

As is known in the art, the operations described above can be performed by hardware, software, or some combination of software and hardware. Various aspects of the example implementations may be implemented using circuits and logic devices (hardware), while other aspects may be implemented using instructions stored on a machine-readable medium (software), which if executed by a processor, would cause the processor to perform a method to carry out implementations of the present application. Further, some example implementations of the present application may be performed solely in hardware, whereas other example implementations may be performed solely in software. Moreover, the various functions described can be performed in a single unit, or can be spread across a number of components in any number of ways. When performed by software, the methods may be executed by a processor, such as a general purpose computer, based on instructions stored on a computer-readable medium. If desired, the instructions can be stored on the medium in a compressed and/or encrypted format.

Moreover, other implementations of the present application will be apparent to those skilled in the art from consideration of the specification and practice of the teachings of the present application. Various aspects and/or components of the described example implementations may be used singly or in any combination. It is intended that the specification and example implementations be considered as examples only, with the true scope and spirit of the present application being indicated by the following claims.

What is claimed is:

1. A method comprising:
    receiving patient feature data;
    determining similarity of pre-stored models with the patient feature data, wherein a database of the pre-stored models is analyzed to assess similarity indicating that feature preparation of the pre-stored models is compatible with the patient feature data;
    for the determination of the similarity indicative of the feature preparation being compatible with the patient feature data:
        conducting the feature preparation for the patient feature data based on the pre-stored model determined to be similar, wherein the feature preparation retrieves reusable features associated with the similar pre-stored model, where the reusable features comprise pre-calculated features of the model and are identified from using a patient identifier to which different types of structured and unstructured data are associated;
        tuning a machine learning model configured to output a prediction probability of a patient condition determine readmission probability using a combination of the pre-stored model determined to be similar and results of the feature preparation and patient feature data;
    wherein determining similarity of pre-stored models further comprises:
        searching the database of reusable models and features based on keys of data sources and feature metadata;
        outputting a similar model list with the pre-stored models based on the search results; and
        in response to determining that a pre-stored model from the similar model list with the maximum similarity satisfies a threshold, returning the similar model list;
    wherein returning the similar model list in response to determining that the pre-stored model from the similar model list with the maximum similarity satisfies the threshold further comprises:
        tuning the similar model to remove reusable features that fail to satisfy a minimum population criteria and a sample data distribution criteria;
        wherein determining similarity of pre-stored models further comprises: in response to determining that the pre-stored models from the similar model list fail to satisfy the threshold, recommending model options for the user to select, and return a model selection based on a user selected model option.

2. The method of claim 1, wherein the prediction probability is for a future patient condition that is used to form a patient treatment plan.

3. The method of claim 1, further comprising providing a data lineage that identifies one or more data sources of data used for the pre-stored model and machine learning model.

4. The method of claim 1, further comprising a user interface to provide a dataset for tests associated with the machine learning model, wherein the dataset comprises at least one of a patient dataset, a medical dataset, a lab dataset, and a doctor's note dataset.

5. The method of claim 1, further comprising creating non-pre-calculated features for other patient feature data determined not to be similar with pre-stored models; and
    joining the pre-calculated features and the created non-pre-calculated features with the patient identifier.

6. The method of claim 1, further comprising outputting a similar model list comprising a model name, a model identifier, a reusable data source, a reusable features, a reusable features path, and a similarity score.

7. The method of claim 1, further comprising outputting a similar model list derived from pre-stored models, wherein the similar model list comprises a user selection for training models.

8. A system comprising:
    a memory;
    a processor coupled to the memory configured to:
    receive patient feature data;
    determine similarity of pre-stored models with the patient feature data, wherein a database of the pre-stored models is to be analyzed to assess similarity indicating that feature preparation of the pre-stored models is compatible with the patient feature data;
    for the determination of the similarity indicative of the feature preparation being compatible with the patient feature data:
        conduct the feature preparation for the patient feature data based on the pre-stored model determined to be similar, wherein the feature preparation retrieves reusable features associated with the similar pre-stored model, where the reusable features comprise pre-calculated features of the model and are identified from a patient identifier to which structured and unstructured data are associated;
        tune a machine learning model configured to determine readmission probability using a combination of the pre-stored model determined to be similar and results of the feature preparation and patient feature data;
wherein to determine similarity of pre-stored models further comprises:
search the database of reusable models and features based on keys of data sources and feature metadata;
output a similar model list with the pre-stored models based on the search results; and
in response to determining that a pre-stored model from the similar model list with the maximum similarity satisfies a threshold, return the similar model list;
wherein to return the similar model list in response to determining that the pre-stored model from the similar model list with the maximum similarity satisfies the threshold further comprises:
tuning the similar model to remove reusable features that fail to satisfy a minimum population criteria and a sample data distribution criteria;
wherein to return the similar model list in response to determining that the pre-stored model from the similar model list with the maximum similarity satisfies the threshold further comprises:
tuning the similar model to remove reusable features that fail to satisfy a minimum population criteria and a sample data distribution criteria;
wherein to determine similarity of pre-stored models further comprises:
in response to determining that the pre-stored models from the similar model list fail to satisfy the threshold, recommending model options for the user to select, and return a model selection based on a user selected model option.

9. The system of claim 8, further configured to create non-pre-calculated features for other patient feature data determined not to be similar with pre-stored models; and
join the pre-calculated features and the created non-pre-calculated features with the patient identifier.

10. The system of claim 8, wherein to provide the prediction probability includes a user interface to display data lineage that identifies one or more data sources of data used for the pre-stored model and machine learning model.

11. The system of claim 8, wherein the data lineage is based on model metadata of the pre-stored models.

12. A non-transitory computer-readable medium storing instructions for a model management system including a processing device configured to:
receive patient feature data;
determine similarity of pre-stored models with the patient feature data, wherein a database of the pre-stored models is to be analyzed to assess similarity indicating that feature preparation of the pre-stored models is compatible with the patient feature data;
for the determination of the similarity indicative of the feature preparation being compatible with the patient feature data:
conduct the feature preparation for the patient feature data based on the pre-stored model determined to be similar, wherein the feature preparation retrieves reusable features associated with the similar pre-stored model that are used to train parameters of the similar pre-stored model, where the reusable features comprise pre-calculated features of the model and are identified from a patient identifier to which structured and unstructured data are associated;
tune a machine learning model configured to determine readmission probability using a combination of the pre-stored model determined to be similar and results of the feature preparation and patient feature data;
wherein to determine similarity of pre-stored models further comprises:
search the database of reusable models and features based on keys of data sources and feature metadata;
output a similar model list with the pre-stored models based on the search results; and
in response to determining that a pre-stored model from the similar model list with the maximum similarity satisfies a threshold, return the similar model list;
wherein to return the similar model list in response to determining that the prestored model from the similar model list with the maximum similarity satisfies the threshold further comprises:
tuning the similar model to remove reusable features that fail to satisfy a minimum population criteria and a sample data distribution criteria;
wherein to return the similar model list in response to determining that the pre-stored model from the similar model list with the maximum similarity satisfies the threshold further comprises:
tuning the similar model to remove reusable features that fail to satisfy a minimum population criteria and a sample data distribution criteria;
wherein to determine similarity of pre-stored models further comprises:
in response to determining that the pre-stored models from the similar model list fail to satisfy the threshold, recommending model options for the user to select, and return a model selection based on a user selected model option.

13. The non-transitory computer-readable medium of claim 12, wherein the prediction is for a future patient condition that is used to form a patient treatment plan.

14. The non-transitory computer-readable medium of claim 12, wherein to provide the prediction includes a user interface to display data lineage that identifies one or more data sources of data used for the pre-stored model and machine learning model, wherein the data lineage is based on model metadata of the pre-stored models.

* * * * *